(12) United States Patent
Bird et al.

(10) Patent No.: US 6,593,084 B2
(45) Date of Patent: *Jul. 15, 2003

(54) CARCINOGEN ASSAY

(75) Inventors: Robert Earl Bird, Rockville, MD (US); Oleg K. Glebov, Germantown, MD (US); Flavia Borellini, Foster City, CA (US); David Jacobson-Kram, McLean, VA (US); Jeffrey M. Ostrove, West Vancouver BC (CA)

(73) Assignee: Robert E. Bird, Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/170,640

(22) Filed: Oct. 13, 1998

(65) Prior Publication Data

US 2002/0086288 A1 Jul. 4, 2002

(51) Int. Cl.$^7$ ............ C12Q 1/68; C12P 19/34; G01N 33/566; C07H 21/04; C07H 19/04

(52) U.S. Cl. ............ 435/6; 435/91; 435/91.2; 436/501; 536/24.3; 536/24.33; 536/26.6

(58) Field of Search ............ 435/6, 91, 91.2; 536/24.3, 24.33, 26.6; 436/501

(56) References Cited

U.S. PATENT DOCUMENTS

| | | | |
|---|---|---|---|
| 5,445,934 A | | 8/1995 | Fodor et al. |
| 5,691,142 A | | 11/1997 | Dahlberg et al. |
| 5,700,637 A | | 12/1997 | Southern |
| 5,712,307 A | * | 1/1998 | Samid ............ 514/538 |
| 5,538,897 A | * | 7/1998 | Yates, III et al. ............ 435/89 |
| 5,830,645 A | * | 11/1998 | Pinkel et al. ............ 435/6 |
| 6,008,045 A | * | 12/1999 | Copeland ............ 435/348 |

FOREIGN PATENT DOCUMENTS

| | | |
|---|---|---|
| EP | 680 517 | 11/1997 |
| WO | WO 97 13877 A | 4/1997 |
| WO | WO 97 27317 A | 7/1997 |
| WO | WO 98 38329 A | 9/1998 |
| WO | WO 99 27090 A | 6/1999 |
| WO | WO 99 32660 A | 7/1999 |
| WO | WO 99 37817 A | 7/1999 |

OTHER PUBLICATIONS

DeRisi et al., "Use of cDNA microarray to analyse gene expression patterns in human cancer", Nature Genetics, vol. 14, pp. 457–460, Dec. 1996.*

Aoki et al., "Alterations in protein synthesis in rat liver cells by in vitro and in vivo exposure to 2,3,7,8–tetrachlorodibenzo–p–doxin", Biochemical Pharmacology, vol. 42 (6), pp. 1195–1201, Apr. 1991.*

McCaffrey et al., "Comparison of effects of direct–acting DNA methylating and ethylating agents on inducible gene expression in vivo", Environmental and Molecular Mutagenesis, vol. 23, pp. 164–170, Dec. 1993.*

Lu, J. et al. "Gene Expression Changes Associated with Chemically Induced Rat Mammary Carcinogenesis", *Molecular Carcinogenesis* (1997) 20(2):204–215.

Jacobson–Kram D "Carcinogenicity Testing in the Future", *Environmental and Molecular Mutagenesis* (1998) 31 (Suppl. 29): 21–26.

Fodor S P A "Massively Parallel Genomics". *Science, US, American Association for the Advancement of Science* (1997) 277 (277):393–395.

Finch J. et al. "Identification of a Cloned Sequence Activated During Multi–State Carcinogenesis in Mouse Skin", *Carcinogenesis* (1991) 12(8): 1519–1522.

PCT/US/9923579 International Search Report.

Bishop "Molecular Themes In Oncogenesis", Cell, (1991) 64:235–248.

Denhardt et al., "The Process of Infection with Bacteriophage X174", J. Mol. Biol. (1965) 12 (3):641–646.

Doty et al., "Strand Separation and Specific Recombination in Deoxyribonucleic Acids: . . . " Proc. Natl. Acad. Sci. *USA* (1960) 46:461.

Gerhardt et al., Manual of Methods for General Bacteriology American Society for Microbiology Press, Washington, D.C. (1981) p. 237.

H. Hennings "Mouse Epidermal Keratinocytes" Keratinocyte Methods, Cambridge University Press (1994) pp. 21–23.

Hayashi et al. "Restriction of In Vivo Genetic Transcription to One of The Complementary Strands of DNA", Proc. Natl. Acad. Sci. *USA* (1963) 50:664.

Isfort et al., "Application of In Vitro Cell Transformation Assays to Predict the Carcinogenic Potential of Chemicals", Mutation Research (1996) 365:161–173.

(List continued on next page.)

*Primary Examiner*—Jeffrey Fredman
*Assistant Examiner*—Arun Kr. Chakrabarti
(74) *Attorney, Agent, or Firm*—Burns, Doane, Swecker & Mathis, L.L.P.

(57) ABSTRACT

The present invention is drawn to methods and assays for the early determination of whether a test agent is a carcinogen. These novel methods and assays are used to correlate the pattern of differential gene expression from mammalian cells treated with the test agent with reference patterns of differential gene expression of mammalian cells treated with known carcinogens. Further, the present invention is drawn to methods of use of DNA and RNA isolated from the treated mammalian cells as well as kits comprising same. The present invention also is drawn to methods of determining whether a test agent is a carcinogen by measuring protein synthesis or post–translational modifications from mammalian cells treated with the test agent compared with mammalian cells treated with a known carcinogen.

23 Claims, 2 Drawing Sheets

OTHER PUBLICATIONS

Lu, J., et al. "Gene Expression Changes Associated with Chemically Induced Rat Mammary Carcinogenesis", Molecular Carcinogenesis (1997) 20: 204–215.

Marmur et al. "Strand Separation and Specific Recombination in Deoxyribonucleic Acids: Biological Studies", Proc. Natl. Acad. Sci. USA (1960) 46:453–461.

Rutberg. S. et al. "Identification of Differentially Expressed Genes in Chemically Induced Skin Tumors", Molecular Carcinogenesis (1997) 20:88–98.

Sager, R. "Expression Genetics in Cancer: Shifting the Focus from DNA to RNA", Proc. Natl. Acad. Sci. USA (1997) 94:952–955.

Schena, M. et al. "Quantitative Monitoring of Gene Expression Patterns with a Complementary DNA Microarray", Science (1995) 270:467–470.

Smith et al., "A Restriction Enzyme from Hemophilus Influenzae", J. Mol. Biol. (1970) 51:379–391.

Southern, "Detection of Specific Sequences Among DNA Fragments Separated by Gel Electrophoresis", J. Mol. Biol. (1975) 98:503–517.

Weinberg, R.A. "How Cancer Arises", Sci. Am. (1996) 275:62–70.

* cited by examiner

Figure 2

P-Primers

P1: 5'-ATTAACCCTCACTAAATGCTGGGGA-3'
P2: 5'-ATTAACCCTCACTAAATCGGTCATAG-3'
P3: 5'-ATTAACCCTCACTAAATGCTGGTGG-3'
P4: 5'-ATTAACCCTCACTAAATGCTGGTAG-3'
P5: 5'-ATTAACCCTCACTAAAGATCTGACTG-3'
P6: 5'-ATTAACCCTCACTAAATGCTGGGTG-3'
P7: 5'-ATTAACCCTCACTAAATGCTGTATG-3'
P8: 5'-ATTAACCCTCACTAAATGGAGCTGG-3'
P9: 5'-ATTAACCCTCACTAAATGTGGCAGG-3'
P10: 5'-ATTAACCCTCACTAAAGCACCGTCC-3'

T-Primers

T1: 5'-CATTATGCTGAGTGATATCTTTTTTTTTTAA-3'
T2: 5'-CATTATGCTGAGTGATATCTTTTTTTTTAC-3'
T3: 5'-CATTATGCTGAGTGATATCTTTTTTTTTAG-3'
T4: 5'-CATTATGCTGAGTGATATCTTTTTTTTTCA-3'
T5: 5'-CATTATGCTGAGTGATATCTTTTTTTTTCC-3'
T6: 5'-CATTATGCTGAGTGATATCTTTTTTTTTCG-3'
T7: 5'-CATTATGCTGAGTGATATCTTTTTTTTTGA-3'
T8: 5'-CATTATGCTGAGTGATATCTTTTTTTTTGC-3'
T9: 5'-CATTATGCTGAGTGATATCTTTTTTTTTGG-3'

CARCINOGEN ASSAY

TECHNICAL FIELD OF THE INVENTION

The present invention is drawn to the field of biotechnology and more specifically to biomedical applications. Further, this invention relates to novel assays for testing whether a compound is a carcinogen. Differential patterns of gene expression for test chemical treated and untreated mammalian cells are compared to those patterns established for known carcinogens.

BACKGROUND OF THE INVENTION

The current "gold standard" for testing whether a compound is carcinogenic is performed with both sexes of two animal species that are treated chronically for two years with a dose of compound at or near the maximum tolerated dose. The end point of the assay is tumor formation. These assays are both expensive and laborious. The aim of this invention is to greatly shorten the time required to determine whether a chemical compound is a carcinogen.

Carcinogens act upon a cell in several ways, with the common result by definition being induction of neoplasia or tumor formation. Carcinogens may be chemical or biological agents. Chemical carcinogens include, for example, compounds of: DMBA; benzo(a)pyrene; dibenzanthracene; acetoxyaminofluoren, methyl N. nitrosogreoxidine; nitroquinoline; dibromomethane; dibromoethane; furan; and 12-O-tetradecanoyil-13-phorbol-acetate (TPA). Biological carcinogens include oncogenic viruses, for example, such as members of the family of papilloma virus. Chemical compounds and biological agents have the shared property that they are each able to cause mutations of the genetic material of an animal cell or otherwise alter the level of expression of non-mutated genes. Despite the different mechanisms of action of carcinogens, these compounds each produce changes in gene expression that occur in the transition from normal to tumor cell. Changes in the transcription level may be detected by differential displays of mRNA isolated from a cell treated with a carcinogen. The changes in the level of translation of the mRNA may also be detected in the differential display of proteins or peptides synthesized in the treated cell.

Differential display of mRNA has been articulated as a means of evaluating the gene expression profile of a cell for the identification of cancer related genes and elucidation of their role in tumorigenesis. For example, more than 100 candidate tumor suppressor genes have been described. (Sager, R., Proc. Natl. Acad. Sci. USA (1997) 94:952–955). Some of these have been identified using differential display of cDNA prepared from isolated mRNA. While more than 100 oncogenes have been identified in animal cells, only a small subset have been found consistently as mutated genes in human cancer (Copper G. M. (1995) Oncogenes; Jones & Bartlett, Seedbury); Weinberg, R. A. Sci. Am. (1996) 275:62–70; and Bishop, J. M. Cell (1991) 64:235–248). The progression of neoplasia development and transformation into malignant tumors is not well understood. However, since cancer genes are defined by their phenotypic expression, research into their differential phenotypic expression has been undertaken as a means to further elucidate the process of carcinogenic induction of tumorigenesis.

For example, carcinogen-mediated changes in cell metabolism may differentially alter the expression of oncogenes, tumor suppressor genes, cell cycle regulators, DNA replication genes (e.g., encoding repair enzymes, receptors), growth factors, stress proteins or known tumor markers. Such differential gene expression may be represented by an increase or decrease of levels of expression or may result in modifications to the gene product expressed, that is, altered forms of proteins, which function differently than proteins in normal cells (e.g., greater or lesser binding affinity; requirement or lack of requirement of co-factors).

Many studies have addressed the changes in genes (mutations) and the changes in gene expression in tumors. These alterations in sequence and synthesis have also been examined as markers of tumorigenesis. However, no one has examined the early changes in gene expression in the first days or weeks after the beginning of treatment with a test compound to determine whether a subset of the changes that occur early in carcinogen treatment are useful to predict whether a tested compound is a carcinogen. The pattern that is developed need not be similar to that in the tumor but need only be predictive of tumorigenic potential.

Seven cDNA fragments of gene transcripts that were overexpressed in mammary carcinomas in the rat model induced by 1-methyl-1-nitrosourea have been identified by differential display of mRNA and molecular cloning (Lu, J., et al., Molecular Carcinogenesis (1997) 20:204–215). However, this research involved the comparison of the latter stage of tumorigenesis (2 months following chemical carcinogenic induction) with control mammary tissue. Lu et al. did not disclose any methods for the differential display of gene transcript fragments associated with the earlier stages of tumorigenesis, that is, prior to actual tumor formation.

Similarly, there are numerous reports in the literature of the identification and role of various oncogenes and tumor suppressor genes. For example, the use of differential display to study gene expression during development of squamous cell carcinomas and the important role played by c-fos (or v-fos) in the transformation to the malignant phenotype in keratinocytes has been reported (Rutberg, S., et al., Molecular Carcinogenesis (1997) 20:88–98). Rutberg et al., as did Lu et al., used the latter stage endpoint of tumor formation in the comparison of differential gene expression in establishing the role of oncogene transformation of epithelial tissue.

There is a clear need for assays which predict at an early stage whether an unknown compound is a carcinogen. Current assays are designed to determine whether an agent is carcinogenic by using one or more surrogate markers. For example, the widely used Ames test represents an analysis of the effects of a test compound upon the frequency of reverse mutation of bacterial test strains, such as the histidine auxotrophic strains of Salmonella typhimurium (Manual of Methods for General Bacteriology, Gerhardt et al, American Society for Microbiology Press, Washington, D.C. (1981) at page 237). This test is not absolute, since a compound under this assay may be mutagenic and not be carcinogenic or alternatively a compound may not evidence mutagenicity in this assay but be carcinogenic as determined using other tests.

Current short-term assays are based mostly on correlation between mutagenic and carcinogenic potential of compound that was established in earlier studies. This correlation is exploited directly in Salmonella mutation assay (Ames test), in the mouse $tk^{+/-}$ assay, and CHO hprf assay. There are also assays based on abilities of carcinogens to interact with DNA or chromatin directly, like DNA adducts assay and single cell gel assay for DNA strand breaks. The mechanisms underlying other assays are less clearly defined, like for micronucleus assay, and cytogenetic assays (FISH, aneuploidy or sister chromatid exchange assays) but are thought to reflect at least in part, the disturbance of the DNA or chromosome organization. These assays show good sensitivity for mutagenic carcinogens but as a rule cannot detect effectively activity of the nongenotoxic carcinogens.

Recently a new test, the Syrian Hamster Embryo (SHE) Cell Transformation assay was developed and refined, which is based on the ability of carcinogens to induce immortalization and transformation (morphological and malignant) of the SHE cells in culture (Isfort and LeBoeuf, *Mutation Research* (1996) 365:161–173). This assay shows good sensitivity and accuracy for mutagenic carcinogens as well as nongenotoxic carcinogens.

Application of the battery of mentioned short-term tests increases the validity of prediction of whether compounds may be carcinogens. However, tumorigenic transformation of a cell in an organism is a result of the complex interaction of the cells with a carcinogen (possibly metabolically activated) and with other cells of the organism. Hence, one should expect that cells may react to a tested compound depending on the cell's phenotypic characteristics, that is, for example, tissue-specific characteristics. Cells of different tissue-specific characteristics may react to the same compound with different outcomes. Considering possible differences in cell response, the enormous variety of industrial, pharmacological, and therapeutic compounds that need to be tested, and further considering the multitude of activation pathways, there is a clear need for a short-term carcinogenicity assay that allows for the evaluation of a cell's response to a compound in different tissues of an organism.

Another more recent approach to assaying the effects of test compounds, at least indirectly upon a cell's genome, employs cells transfected with genetic constructs comprising selected "stress promoters" that are induced by specific stress factors, such as "DNA stress" which includes damage to DNA strands by chemicals or UVA radiation (Farr, S., et al., EP 0 680 517 (1997)). In this assay, the transformed cell is exposed to potentially toxic compounds and the levels of transcription of one or more heterologous reporter genes, each of which is operatively linked to its respective stress promoter, is assayed for transcription by hybridization of probes specific to the mRNA of each reporter gene. This assay indirectly measures whether a potentially toxic compound will induce a stress promoter to permit transcription of its reporter gene. Farr et al. discloses the creation of a "stress induction profile" for each compound by classifying which stress promoters are induced for each compound tested. This method indirectly measures toxicity by the use of artificial gene constructs of selected "stress promoters" and selected reporter genes as they are transfected into specific host cells. Further, this method measures through hybridization whether an mRNA transcript of a reporter gene is expressed by a stress promoter that responds to toxic agents. Since the stress promoter is fused out of context to the reporter gene, this method does not measure the functionality of the transcript or translated protein product. Since Farr et al. transformed HepG2 cells in their assay, these artificial gene constructs may provide different outcomes if the constructs are used to transform different host cells or host cells of different tissues. Still wanting is a method that measures differential expression of native genes on a wider scale and in the short period following exposure of the target cell to the test compound.

The high-throughput methods (based mostly on using high-density gene arrays) developed in recent years, will be exploited to establish patterns of gene expression changes that are diagnostic for response to known carcinogens of the different mouse tissue cells. These patterns will serve as a basis for a new short-term assay for detecting carcinogenic potential of chemical and biological compounds.

A high-capacity quantitative method of differential gene expression that uses hybridizable cDNA arrays robotically printed on glass was reported by Schena, M., et al., *Science* (1995) 270:467–470. This method fixes to a substrate amplified cDNA prepared from both complete gene sequences and from partial sequences or expressed sequence tags (ESTs). Fluorescent hybridization probes were prepared from total mRNA and used to identify corresponding cDNA. This methodology was able to clearly identify the overexpression of a single target gene.

In contrast, currently available assays for carcinogenesis either operate in bacterial test systems, which do not accurately reflect mammalian cellular response, or require a significant amount of time to demonstrate phenotypic expression of carcinogen activity in mammalian whole animal models. The present invention is able to quickly identify carcinogen activity by effects upon differential gene expression in mammalian cells or animals at a point in time prior to tumor formation by comparing these differential levels of expression with prior determined patterns of differential genetic expression caused by known carcinogens.

SUMMARY OF THE INVENTION

The present invention provides an assay for the early detection of carcinogenesis by measuring the net changes in gene expression that result from the treatment of a mammalian cell or whole animal with a test agent over those of a control cell or control whole animal further compared with previously determined reference patterns of genetic expression altered by known carcinogens. The present invention further provides methods and kits to identify a carcinogen. The present invention also provides for methods for identifying DNA and proteins related to carcinogenesis. Additionally, the present invention contemplates the DNA and proteins related to carcinogenesis that are identified by the methods and assays of the present invention and that are predictive that a test agent or substance is a carcinogen.

More specifically, one embodiment of this present invention provides assays and methods comprising the steps of: a) preparing cDNA from RNA isolated from mammalian cells treated with a test agent for less than about two years, wherein said cDNA is detectably labeled; b) determining a pattern of expression by assessing the ability of said labeled cDNA to hybridize to each of a multiplicity of nucleotide sequences arrayed on a substrate; c) determining reference patterns of differential gene expression by assessing the ability of a second labeled cDNA to hybridize to each of a multiplicity of nucleotide sequences, wherein said second labeled cDNA is prepared from RNA isolated from mammalian cells treated with a known carcinogen for less than about two years; and d) comparing similarities in patterns of expression from cells treated with a test agent to reference patterns from cells treated with a known carcinogen.

A preferred embodiment provides that RNA is isolated from mammalian cells treated with a test agent or known carcinogen for less that about six months. A further preferred embodiment provides that RNA is isolated from mammalian cells treated less than about two weeks or more preferably treated for less than about two days.

In another preferred embodiment, the test cDNA may be labeled with a fluorescent molecule emitting one wavelength of light and the control cDNA labeled with a second fluorescent molecule emitting a second wavelength of light. The hybridization results that form a pattern of expression and clearly represent effects of treatment of mammalian cells with a test agent or substance will always thus be controlled internally. Other preferred embodiments include the use of other similarly detectable labels, that include but are not limited to: radioisotopes; enzymes; antigens or antibodies.

Another embodiment of the present invention is a method to identify a test substance as a carcinogen, which method includes: a) providing cDNA derived from mammalian cells that have been contacted with the test substance for less than about two years; b) determining a first pattern of hybridization of the cDNA with respect to a multiplicity of nucleotide sequences; and c) comparing the pattern with a corresponding second pattern obtained at a corresponding time after the cells have been contacted with a known carcinogen, whereby a similarity in the first and second patterns identifies the test substance as a carcinogen. A preferred embodiment provides that the cDNA is obtained from cells that have been contacted with the test substance or a known carcinogen for less that about six months. A further preferred embodiment provides that the cDNA is obtained from cells contacted for less than about two weeks or more preferably contacted for less than about two days.

Another aspect of the present invention provides an assay kit for identifying a test substance as a carcinogen, comprising: a) reagents for the preparation of cDNA prepared from RNA isolated from mammalian cells treated with a test substance for less than about two years; b) reagents for the preparation of cDNA prepared from RNA isolated from mammalian cells treated with a known carcinogen for less than about two years; c) DNA sequences arrayed on a substrate that are hybridizable to the cDNA; and d) label suitable for the detection of the DNA sequences hybridized to the cDNA; wherein the identification of a test substance as a carcinogen is achieved by creating a first pattern of differential gene expression using cDNA prepared from the RNA isolated from mammalian cells treated with a test substance for less than about two years and comparing the first pattern with a corresponding second pattern obtained at a corresponding time after the cells have been contacted with a known carcinogen, whereby a similarity in the first and second patterns identifies the test substance as a carcinogen.

Yet another aspect of this invention provides an assay for early detection of carcinogenesis, comprising the steps of: a) selecting a protein isolated from mammalian cells treated with a test agent for less than about two years; b) measuring differences in protein synthesis or post-translational modification; and c) determining whether the test agent is carcinogenic by comparing differences in protein synthesis or post-translational modification to protein isolated from mammalian cells treated with a known carcinogen for less than about two years. In a preferred embodiment, this invention provides that the differences in protein synthesis or post-translational modification are measured by electrophorectic gel analysis and that the protein is detectably labeled. Such detectable labels, include but are not limited to: a fluorescent dye; radiolabelled compound; or enzymatically detectable label, for example, horse radish peroxidase or alkaline phosphotase.

One other embodiment of the present invention provides that differences in protein synthesis or post-translational modification are measured by enzymatic digestion of protein and mass spectrometry analysis.

In another embodiment, this invention contemplates that the mammalian cells are treated with a carcinogen in vitro. In still another embodiment, this invention contemplates that the mammalian cells are treated with a carcinogen in vivo. Still another preferred embodiment, this invention provides that the differential gene expression is selected from the group consisting of genes whose level of expression is increased; genes whose level of expression is decreased; genes that are expressed and genes that are not expressed.

Another aspect of the present invention provides for methods of identifying genes, genetic sequences and proteins related to carcinogenesis as well as the genes, genetic sequences and proteins identified by the methods of this invention. A further aspect of the present invention provides for the reference patterns of differential gene expression of mammalian cells treated with a known carcinogen. Another embodiment of the present invention provides for protein measure by any one of the methods disclosed. A still further aspect of the present invention includes DNA or a DNA sequence as used in any of the methods provided herein, where the DNA or DNA sequence is predictive that a test agent or test substance is a carcinogen.

Additional aspects of the present invention relate to the use of substrates as contemplated herein. A preferred embodiment of the present invention provides for a multiplicity of nucleotide sequences arrayed on a substrate. A still further preferred embodiment contemplates substrates selected from the group consisting of: membrane filter; glass; ceramic; and solid organic polymer.

The present invention further contemplates the use of one or more assays or methods as discussed supra and further disclosed herein used in combination with one another. For example, a preferred embodiment includes the steps of: preparing a first cDNA from a first mRNA; isolated from mammalian cells treated with a test agent for less than about two years, wherein the first cDNA is detectably labeled; determining a pattern or expression by assessing the ability of the labeled cDNA to hybridize to each of a multiplicity of nucleotide sequences arrayed on a substrate; determining reference patterns of differential gene expression by assessing the ability of a second labeled cDNA to hybridize to each of a multiplicity of nucleotide sequences, wherein the second labeled cDNA is prepared from a RNA isolated from mammalian cells treated with a known carcinogen for less than about two years and comparing similarities in patterns of expression from cells treated with a test agent to reference patterns from cells treated with a known carcinogen. This assay further comprises the steps of: selecting a protein isolated from the same mammalian cells treated with the same test agent for less than about two years; measuring differences in protein synthesis or post-translational modification; and determining whether the test agent is carcinogenic by comparing differences in protein synthesis or post-translational modification to protein isolated from mammalian cells treated with a known carcinogen for less than about two years. In a preferred embodiment, this invention provides that the differences in protein synthesis or post-translational modification are measured by electrophorectic gel analysis and that the protein is detectably labeled.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

BRIEF DESCRIPTION OF THE DRAWINGS

FIG. 2 shows P & T Primers used in polymerase chain reaction.

DETAILED DESCRIPTION OF THE INVENTION

Figure 1:
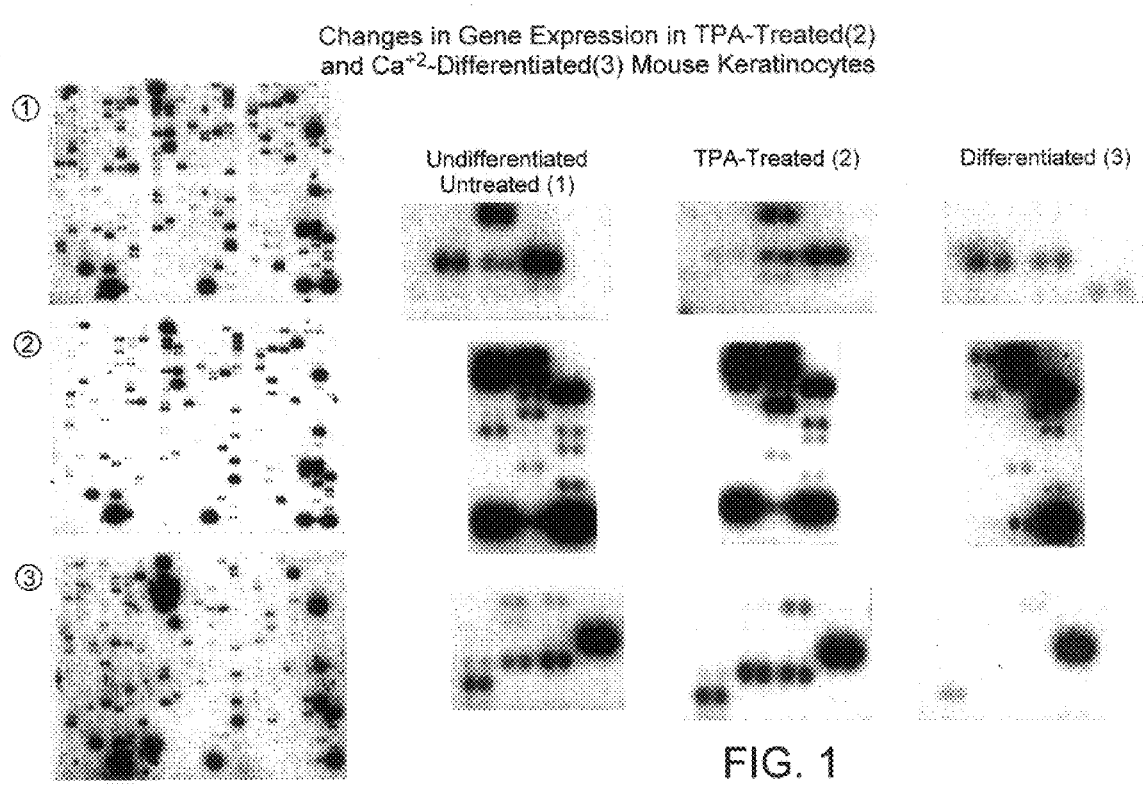
FIG. 1 shows changes in gene expression in TPA-Treated and calcium differentiated mouse keratinocytes.

The above and various other objects and advantages of the present invention are achieved by preparing a differential display of genetic expression for cells treated with a test agent compared with reference patterns of differential gene expression of mammalian cells treated with one or more carcinogens.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated in their entirety herein by reference.

For example, what is meant by carcinogenesis is the origin or initiation or production of neoplasia or tumor formation. Neoplasia is meant to include both benign and malignant growth of new tissue. Such neoplasia may include, but is not limited to: carcinoma, sarcoma, lymphoma, blastoma, and mesothelioma. A test agent is any molecule, compound or biological organism that is selected to be used with the methods, assays or other embodiments of the present invention. The test agent may be modified or altered to facilitate carcinogenicity. Further, the use of the term carcinogen is intended to include carcinogenic agent. Mammalian cells include both cultured cell lines as well as cells isolated from mammalian tissues.

Conditions for the hybridization of DNA are readily available to one in the art. Such conditions include those as provided in Denhardt et al., *J. Mol. Biol.* 12(3):641–646 (1965) or in Dabbler, et al., (U.S. Pat. No. 5,691,142), which is incorporated in its entirety herein by reference. The detection of specific nucleic acid sequences or a multiplicity of nucleotide sequences as present in oligonucleotides has been achieved typically by hybridization. Hybridization methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad Sci. USA* 46:453 (1960) and Doty et al., *Proc. Natl. Acad. Sci. USA* 46:461 (1960) have been followed by the refinement of this process into an essential tool of modern biology. Initial hybridization studies, such as those performed by Hayashi et al, *Proc. Natl. Acad. Sci. USA* 50:664 (1963), were formed in solution. Further development led to the immobilization of the target DNA or RNA on solid supports. With the discovery of specific restriction endonucleases by Smith and Wilcox, *J. Mol. Biol.* 51:379 (1970), it became possible to isolate discrete fragments of DNA. Utilization of immobilization techniques, such as those described by Southern, *J. Mol. Biol.* 98:503 (1975), in combination with restriction enzymes, has allowed for the identification by hybridization of single copy genes among a mass of fractionated, genomic DNA.

What is meant by differential gene expression is, for example, but is not limited to, a method to evaluate the expression of the genes of a cell. Such differential gene expression may be represented as an increase or decrease in the levels (including non-detectable levels) of transcription of genes by the synthesis of mRNA. Differential gene expression may also be represented as an increase or decrease in the levels (including non-detectable levels) of translation of mRNA coding for a gene in the synthesis of a protein or peptide. Also, differential gene expression may include post-translational modification of the protein or peptide sequence as well as mutated forms of the protein or peptide gene product.

What is meant by reference patterns of differential gene expression is the physical manifestations of differential gene expression. Such patterns may take the form of films or gels or data records or other tangible representations of hybridizations of genetic fragments or levels of protein or peptide synthesis that are created by determining the changes in genetic expression of mammalian cells that have been treated with known carcinogens.

What is meant by referring to mammalian cells as pre-tumorous cells is that the cells have not yet demonstrated tumor formation or unregulated growth.

I. Differential Genetic Expression Array

The present invention contemplates that the reference patterns of differential gene expression of this assay could include as few as several sequences and up to thousands. The selection of genes may be made by simply choosing known oncogenes, tumor suppressor genes, cell cycle regulation genes, and DNA replication genes (encoding repair enzymes, receptors) growth factor genes, stress proteins or known tumor marker genes. While one may determine to screen all known EST's in databases known to the art, it is more likely that sufficient sequences, to define a pattern or patterns of gene synthesis change, will be found by only screening a fraction of the known sequences. It is not necessary to detect every change but rather to detect a number of changes that are sufficient to establish a reference pattern that is useful in distinguishing a carcinogen from other non-carcinogenic compounds. The number of sequences that are contemplated for selection may range between three to 1000 and preferably from 10 to 200 and more preferably from 20–100.

The present assay will detect changes in gene expression early in a treatment protocol. These changes may occur in subsequent tumors caused by the carcinogen but this is not a necessary finding. The important changes may be transitory and our experiments are designed to detect them. We anticipate that the important changes occur in treated animals from as few as a single treatment to five doses per week for up to 90 days. We wish to shorten the time that animals are treated as much as possible.

Initially test cDNA is prepared from RNA obtained from tissue of animals treated with a test agent, where in order to create reference patterns, test agents will be carcinogens. The reference will be cDNA prepared from RNA of control animals of the same age, sex, and protocol that have not been treated with a test agent but with the vehicle alone. An ideal version of the assay could be the selection of a set of cell lines that show a pattern of gene synthesis, which is a diagnostic of a carcinogen. This would eliminate the use of animals completely for our assays.

II. Use of cDNA hybridization patterns

Once the set of gene sequences to be used in our tests has been selected we contemplate that assays may be performed using one of several formats. (1) Gene sequences to be tested could be immobilized on a substrate, such as silicon, glass or other suitable surface or sequences may be synthesized in place on the surface. Many such substrates are commonly referred to as chips or gene chips. The first cDNA probe, labeled with one detectable label such as a fluorescent molecule, is prepared from RNA extracted from a tissue from a treated animal. The second cDNA probe prepared from RNA extracted from the same tissue from a matched control animal and labeled with a second detectable label, such as a second fluorescent molecule. These probes are hybridized to the cDNA or oligonucleotides on the chip. After hybridization, the relative amount of the detectable labels, for example the fluorescence, is measured over each spot of cDNA and this measurement is corrected for housekeeping cDNA sequences on the same chip. Housekeeping cDNA sequences are used as a control to normalize data. The differences in synthesis, either increased or decreased relative to the control, define the pattern of synthesis or gene expression. The observed pattern is compared to our database to determine whether it resembles a pattern associated with known carcinogens. Housekeeping genes are sequences such as β-actin cDNA because β-actin is assumed to be synthesized in both treated and untreated animals. We are not limited to β-actin as a control and can use any sequence, which is synthesized at the same levels in both tissues. Hybridization results are internally controlled by labeling the test cDNA using one detectable label that is distinguishable over the second detectable label, for example, by labeling the test cDNA with a fluorescent molecule emitting one color of light and the control cDNA labeled with a second fluorescent molecule emitting a second distinguishable color.

(2) A second method would be to fix an array of cDNA on a glass slide or other ceramic substrate. The labeling, hybridization, and analysis are performed similarly to that described supra in order to determine the pattern of synthesis for a sample. An array of DNA sequences could easily be prepared using techniques available to one of skill in the art. For example, U.S. Pat. No. 5,445,934 teaches a method and apparatus for preparation of a substrate containing a plurality of sequences. Photoremovable groups are attached to a surface of a substrate. Selected regions of the substrate are exposed to light so as to activate the selected areas. A monomer, also containing a photoremovable group, is provided to the substrate to bind at the selected areas. The process is repeated using a variety of monomers such as amino acids until sequences of a desired length are obtained.

Detection methods and apparatus are also disclosed. Also, U.S. Pat. No. 5,700,637 teaches an apparatus and method for analyzing a polynucleotide sequence; either an unknown sequence or a known sequence. A support, e.g. a glass plate, carries an array of the whole or a chosen part of a complete set of oligonucleotides which are capable of taking part in hybridization reactions. The array may comprise one or more pair of oligonucleotides of chosen lengths. The polynucleotide sequence, or fragments thereof, are labeled and applied to the array under hybridizing conditions. Applications include analyses of known point mutations, genomic fingerprinting, linkage analysis, characterization of mRNAs, mRNA populations, and sequence determination.

A multiplicity of nucleotide sequences arrayed on a substrate may also be commercially available, for example, from Clontech Laboratories.

(3) A third method would be to denature and array the cDNA sequences for our set of test sequences on two sets of membrane filters. Radiolabeled cDNAs are prepared from the test RNA and the control and each is hybridized to a set of membrane filters.

After washing, the filters are either exposed to x-ray film or analyzed in a phosphoimaging system to measure the amount of cDNA hybridized to each set of membranes. The hybridization is normalized for housekeeping genes and the pattern of synthesis determined by the relative radioactivity over each cDNA. This determination is made by comparing a test filter with its control counterpart. A further alternative is to employ two separate radioisotopes for labeling the cDNA prepared from test RNA and cDNA prepared from the control RNA.

The skilled artisan would readily appreciate from the present disclosure, that other detectable labels, including enzymes, such as horse radish peroxidase or alkaline phosphotase may be used accordingly.

III. Use of Protein Synthesis Patterns

The present invention further contemplates that the changes in translation of genetic sequences as well as the changes in transcription of genes, as has been discussed supra, may be used as a measure or characteristic of whether a test agent functions as a carcinogen. Changes in the amounts or levels of expression of the genetic end products—proteins—as translated from the mRNA of mammalian cells may also be determined. However, the present invention should not merely be limited to the detection of differences in the level of protein synthesis, either increased or decreased, in a tissue from treated animal cells since postranslational modification could also be affected by carcinogen treatment. These postranslational modifications include: cleavage of the protein into smaller units; degradation to short peptides or amino acids; phosphorylation; alkylation; deamidation; glycosylation; as well as any other postranslational modifications of the synthesized proteins.

The methods available to measure difference in protein synthesis or postranslational modifications are well known in the art. For example, two dimensional polyacrylamide gel electrophoresis separates proteins or peptides by net charge in the first direction and by size in the second. Proteins or peptides are visualized by staining or autoradiography and analyzed using image analysis software.

Proteins can be displayed by two-dimensional gel electrophoresis. A sample of protein to be displayed is loaded onto an isoelectric focusing gel and the proteins allowed to reach equilibrium. A lane of this gel, narrow strip, or tube gel is laid on top of an SDS Page slab gel and the proteins previously separated by isoelectric point now are separated by size. The proteins thus displayed can be detected by staining or by autoradiography if previously radiolabeled. Clearly the proteins displayed from any sample will depend on the sample preparation, pH range of the focusing gel, and the polyacrylamide concentration of the size separation gel.

The proteins differentially expressed early in test compound treatment can be identified by comparing two dimensional gels run on proteins extracts of tissues from treated and untreated animals. A protein that is overexpressed upon treatment will show up as a stronger spot on the treated gel and underexpressed proteins will be lighter than the corresponding control spot. The protein in question can be further identified by trypsin (or other specific cleavage treatment) and analysis by mass spectrometry. The precise molecular weights of the peptides can be matched to peptide databases to make the identification. If one peptide appears in more than one protein, additional peptides can be analyzed to complete the identification.

An alternate method of analyzing proteins would be through the use of mass spectroscopy to characterize proteins or peptides by their mass. This characterization could be coupled to a method of separation of proteins, including capillary electrophoresis or liquid chromatography. The separation or filtration step or the two dimensional gels above, will limit the number of proteins or peptides characterized at any one time. Furthermore, the filtering step may be designed to emphasize those proteins most changed by the treatment with a carcinogen. Identification would be made by searching a molecular weight database.

Additional filtering steps could be followed in the method of initial extraction of the proteins or peptides. Rather than examining the total proteins synthesized in a tissue, selected fractions could be analyzed. Such fractions may include: the isolation of soluble fractions; membrane fractions; salt precipitate fractions; or fractions obtained by any other treatment.

Clearly the characterization of carcinogens by protein changes, either alterations in synthesis or modifications, will yield reference patterns of differential genetic expression or changes that are characteristic of carcinogens. These reference patterns may characterize a new carcinogenic agent if the pattern resulted from treatment of animal cells with the new agent.

Having now generally described the invention, the same will be more readily understood through reference to the following examples which are provided by way of illustration, and are not intended to be limiting of the present invention, unless specified.

EXAMPLE 1

Gene Expression Changes in TPA-Treated and Terminally Differentiated Primary Mouse Keratinocytes Cultures 1. Primary mouse keratinocytes cultures Cultures of newborn mouse keratinocytes were established essentially as described by H. Hennings (In *Keratinocyte Methods,* Cambridge University Press (1994), pages 21–23). Briefly, mice two to three days postpartum were sacrificed by metaphane narcosis, rinsed in 70% ethanol, and kept on ice. Skins were peeled off, stretched out and floated (with epidermis facing upward) on the surface of a 0.25% trypsin solution in $Ca^{+2}$, $Mg^{+2}$ free PBS overnight at 4° C. Skins were transferred to a sterile surface, the epidermis was separated from dermis, the epidermis was minced, and the mixture stirred in serum-free keratinocyte growth medium (KGM, Clonetics). This cell suspension was filtered through nylon gauze, cells were centrifuged (2,000 rpm for 5 min), resuspended in KGM with 20 $\mu$M $Ca^{+2}$ (20 KGM), and then the cells were counted and plated (approximately $2 \times 10^6$ per 10 cm plate coated with mouse collagen type IV in 20 KGM) and the cell cultures were incubated at 37° C. with a 7% $CO_2$. After 16–24 hours, cells were washed in $Ca^{+2}$, $Mg^{+2}$ free phosphate buffered saline (PBS), and cultivated on 20 KGM, with the cell culture medium changed (that is, old medium discarded and fresh medium provided) each other day. For induction of terminal differentiation, medium was changed, usually on the sixth day of cultivation of the keratinocytes, to KGM containing 1.2 mM $Ca^{+2}$, and the keratinocytes were cultivated for 24 hours before RNA isolation.

For phorbol-myristate acetate (TPA) treatment, keratinocyte cultures were fed with 20 KGM containing 0.1 $\mu$g/ml of 12-O-tetradecanoyil-13-phorbol-acetate for 24 hours, before isolation of RNA.

2. Differential display of mRNAs synthesized in control keratinocytes, $Ca^{++}$ differentiated keratinocytes and TPA-treated keratinocytes.

Total RNA was isolated by acid phenol procedure using TRI Reagent™ (Molecular Research Center, Inc.) and according to manufacturer's instructions from (1) terminally differentiated keratinocytes, cultivated in KGM medium containing 1.2 mM $Ca^{+2}$ for 24 hours; (2) TPA-treated keratinocytes, cultivated in KGM containing 20 $\mu$M $Ca^{+2}$ and 0.1 $\mu$g/ml TPA for 24 hours; and (3) control keratinocyte cultures fed 24 hours before RNA isolation with 20 KGM containing, in some experiments, 0.05% DMSO (dimethyl sulphoxide).

Differential display of total RNAs from keratinocyte cultures (1), (2), and (3) was performed with Delta-RNA Fingerprinting Kit™ (Clontech) according to the manufacturer's instructions. Briefly, cDNAs were synthesized from total RNAs using Murine Moloney Leukemia Virus (MMLV) reverse transcriptase. Two dilutions of cDNA were prepared (diluted 10-fold and 40-fold). Each total RNA sample was used to synthesize cDNA that was amplified using polymerase chain reaction (PCR) methodology using P & T primers in presence of $[\alpha\text{-}^{33}P]$ dATP. These primers are listed in FIG. 2. The labeled amplified bands were displayed on sequencing gels and the differential appearance of labeled bands for each primer pair was examined. The appearance of a band from a sample that was not present in the control lane indicated overexpression and the disappearance or reduction in intensity of a band indicated suppression of synthesis. The candidate bands were cut from the sequencing gel and reamplified using the original primer pairs. Following electrophoresis on agarose gels, reamplified DNA fragments were cut out and purified using a QIAEX II gel extraction kit™ (QIAGEN). The DNAs were labeled and used to confirm the differential expression by hybridization with Northern blots of Poly $(A)^+$ containing RNA isolated from total RNAs (1), (2), and (3). Equal quantities of these RNAs were electrophoresed on agarose gels and blotted to nitrocellulose filters. Equal loading of RNA was confirmed by hybridization with a $\beta$-actin probe, whose mRNA was assumed to be present in approximately equal amounts in all of the preparations. The blots were stripped of radiolabel and then used to confirm the differential synthesis of a fragment. Upon confirmation, the fragment was cloned into pCRII using the TA cloning kit™ (Introvitrogen). Cloned DNA fragments were sequenced with SequiTerm Excel II kit™ (Epicentre Technology).

The genes or ESTs identified by differential display are presented in Table 1.

TABLE 1

Differentially Expressed Genes in TPA Treated Keratinocytes, Identified By Differential Display and Northern Blot Hybridization

| Gene | Size of Cloned Fragment, bp | Changes in Expression (Comparative to Untreated cells) | Known Homologous Sequence |
|---|---|---|---|
| 110176/4 | 200 | Suppressed in TPA-Treated Cells | Mouse Cytokeratin Endo A (156/156; 100%) |
| 2672/1 | 550 | Suppressed in TPA-Treated Cells | Mouse ESTs AA492919 (124/127; 97%), AA607761 (93/97; 95%); Human Dnase 1 Homologue HS U62647 (41/53; 77%) |
| 31777 | 650 | Overexpressed in TPA-Treated Cells | Mouse EST AA073833 (67/67; 100%) |
| 19102/3 | 320 | Overexpressed in CA + 2-Treated ans Suppressed in TPA-Treated Cells | Mouse ESTs AA038613 (251/251; 100%), W14382 (212/213; 99%) |

TABLE 1-continued

Differentially Expressed Genes in TPA Treated Keratinocytes,
Identified By Differential Display and Northern Blot Hybridization

| Gene | Size of Cloned Fragment, bp | Changes in Expression (Comparative to Untreated cells) | Known Homologous Sequence |
|---|---|---|---|
| 3177715 | 650 | Suppressed in TPA-Treated Cells | Mouse ESTs AA423711 ((156/156; 100%), and AA637015 (96/98; 97%) |
| 83442 | 550 | Overexpressed in TPA-Treated Cells | Mouse Connexin 26 (160/161; 99%) |
| 31774/6/8 | 650 | Suppressed in TPA-Treated Cells (6 kb RNA) | Mouse ESTs AA423711 (186/186; 100%), W82493 (198/203; 97%; and 52/53; 98%, AA63700159132/134; 98%) |
| 4314 | 1000 | Overexpressed in TPA- and Ca + 2-Treated Cells | AA109991 (200/201; 99%), AA561914 (200/201; 99%) AA067670 (139/140; 99%), AA864127 (133/134; 99%) |
| 2552/4 | 650 | Suppressed in TPA-Treated Cells (5.5 kb RNA) | ND |

3. Hybridization of cDNA to filters containing mouse DNA sequences

Atlas™ Membranes (Clontech) contain mouse cDNA in paired spots. Each pair cDNA, included gene sequences from known oncogenes, tumor suppressors, cell cycle regulators, stress response genes, ion channels and transporters, intracellular signal transducers, apoptosis genes, DNA synthesis, DNA repair, DNA recombination, transcription factors, general DNA binding proteins, receptors, cell surface antigens, cell adhesion, cell-cell communication, cytoskeleton, mobility, protein turnover, and housekeeping proteins. Each membrane filter contained 588-mouse cDNA's, as well as nine housekeeping control cDNAs, and negative control sequences. We have used pairs of these filters to select additional gene sequences, which are differentially expressed in the keratinocytes.

Poly(A)$^+$, containing RNAs were prepared from total RNAs isolated from control (untreated), TPA-treated and terminally differentiated primary mouse keratinocytes as discussed supra. Labeled cDNAs were synthesized with reagents provided in the Atlas™ Kit (Clontech) and used for hybridization with Atlas™ membranes (Clontech) according to manufacturer instructions. An experimental cDNA was always compared to control cDNA. The filters were washed and exposed to X-ray films for varying lengths of time. Estimation of equal hybridization to housekeeping genes was used as normalization so that gene sequences that are over or under-expressed could be determined by the difference in intensity of the same spots on an experimental filter and a control.

Two and three technicians analyzed sets of radioautograms exposed to pairs of Atlas™ membranes (ClonTech) hybridized to experimental and control cDNAs and showing equal signals for housekeeping genes. Only genes that were consistently identified as overexpressed or suppressed genes comparing control radioautograms, as shown in FIG. 1, are provided in Tables 2 and 3.

TABLE 2

Differentially Expressed Genes In TPA Treated Keratinocytes,
Identified by Hybridization With Atlas ™ cDNA Array(s) (Membranes)

| Overexpressed Genes | Suppressed Genes |
|---|---|
| p53 protein | Tumor suppressor maspin |
| TSG101 tumor susceptibility protein | cErbA oncogene; Thyroid hormone receptor |
| RNA Polymerase I termination factor TTF-1 | cJun proto-oncogene |
| Cot proto-oncogene | c-myc proto-oncogene |
| CSF-1; colony stimulating factor 1 | IGFBP-2; insulin-like growth factor binding protein 2 |
| Cdk4 | p18inc4; cdk4 and cdk6 inhibitor |
| Oxidative stress-induced protein | Golgi 4 transmembrane spanning transporter |
| I-Kappa B alpha chain | Glucose transporter-1 |
| Protein kinase C theta type | Interleukin-6 receptorbeta chain |
| Transducin beta-2 subunit | STAT6; (IL-4 Stat) |
| Bax protein; homologue of Bcl-2 | Syp; adaptor protein tyrosine phosphatase |
| GST Pil; glutathione S-transferase Pi 1 | Gluthathione S-transferase (microsomal) |
| Chop 10; homologue of Gadd153 | Gluthathione S-transferase Mul |
| TDAG51; couples TCR signaling to Fas expression | Proteine tyrosine phosphotase |
| Activating transcription factor 4 | Butyrate response factor 1 |
| Homeo box protein 8 | CACCC Box binding protein BKLF |
| CD44 antigen | DP-1 (DRTF-polypeptide 1) cell cycle regulatory transcription factor |
| Integrin alpha 2 | HMG-14 |
| Integrin beta | Dystroglycan 1 |
| VLA-3 alpha subunit | Follistatin |
| Inhibin beta subunit | Cytokeratin 1 |
| Cytokeratin 18 | TIMP-3 tissue inhibitor of metalloproteinase 3 |
| Cathepsin | |

TABLE 3

Differentially Expressed Genes is Terminally Differentiated Keratinocytes
Identified by Hybridization With Atlas ™ cDNA Array Membranes

| Overexpressed Genes | Suppressed Genes |
|---|---|
| Ezrin (Villin 2) | Tumor suppressor maspin |
| ZO-1 (Tight junction protein) | c-myc proto-oncogene |
| Cot proto-oncogene | Cyclin G |
| Casein kinase II (alpha Subunit) | Prothymosin alpha |
| N-ras proto-oncogene | BST-1; CD38 antigen |
| p18ink4; cdk4 and cdk6 inhibitor | GST Pi 1; glutathione S-transfererase Pi 1 preadipocyte growth factor |
| Glutathione reductase | DAD-1; defender against cell death 1 |
| CACCC Box-binding protein | SP13; serine proteinase inhibitor |
| Homeobox protein 8 | MHR23B; Rad23 homologue |
| Retinoic acid binding protein II (CRABP-II) | Ubiquitin-conjugating enzyme |
| Insulin-like growth factor binding protein-1 (IGFBP-1) | YY1 (UCRBP) transcription factor |
| Cytokeratin 18 | CD44 antigen |
| | Dystroglycan 1 |
| | Neuroleukin |
| | Cytokeratin 14 |
| | Cathepsin H |
| | Cathepsin L |

4. cDNA subtraction and hybridization with Atlas™ membranes (Clontech)

cDNAs were synthesized from poly(A)$^+$ RNA isolated from untreated control and TPA-treated mouse keratinocytes and subtracted using PCR-Select™ cDNA subtraction kit (Clontech) following by the manufactures instructions. cDNA from TPA-treated keratinocytes that was subtracted against cDNA from untreated cells was labeled by random primer labeling protocol and used in hybridization studies on Atlas™ cDNA membranes. These studies identified genes that were overexpressed in TPA-treated keratinocytes. Similarly, cDNA from control keratinocytes was subtracted against cDNA from TPA-treated keratinocytes. Varying the time of film exposure, normalized hybridization signals for housekeeping genes were obtained and autoradiograms were analyzed by two technicians. A list of genes overexpressed and suppressed upon TPA treatment of mouse primary keratinocytes is shown in Table 4.

TABLE 4

Differentially Expressed Genes in TPA Treated Keratinocytes Identified by Hybridization of the Subtracted cDNAs with Mouse Atlas ™ cDNA Array Membranes

| Overexpressed Genes | Suppressed Genes |
| --- | --- |
| BST-1; lymphocyte differentiation antigen CD38 | c-ErbA oncogene (Thyroid hormone receptor) |
| I-Kappa B alpha chain | H-ras proto-oncogene |
| Rac 1 murine homologue | Cyclin D1 |
| Zyxin; LIM domain protein; -actin binding protein | Cyclin D2 |
| Bax protein (Bcl-2 homologue) | Prothymosin alpha |
| GST Pi 1; glutathione S-transferase; preadipocyte growth factor | Hsp27; heat shock 27KD-protein 1 |
| c-Act proto0 oncogene; Rac-alpha; proteine kinase B | Dystroglycan 1 |
| Nuclear factor related to p45 NF-E2 | Insulin-like growth factor binding protein 6 (IGFBP 6) |
| Monocyte chemoattractant protein 3 | TIMP-3 tissue inhiditor of metalloproteinases-3 |
| Interleukin-2 receptor gamma chain | |
| CD18 antigen beta subunit | |
| CD44 antigen | |
| CD14 antigen | |
| Glutamate receptor channel subunit gamma | |
| Bone morphogenetic protein 1 | |
| Macrophage inflammatory protein | |
| Macrophage inflammatory protein 1 (Act2) | |
| Macrophage inflammatory protein 2 alpha | |
| Interleukin 1Beta | |
| Cytokeratin 14 | |
| Cytokeratin 1 | |
| Cathepsin L | |
| Collagenase type IV | |
| Plasminogen activator inhibitor-2 | |
| Serine protease inhbitor 2 (spi-2) | |

EXAMPLE 2

Gene Expression Changes in Skin and Liver of DMBA-Treated Mice

1. Skin treatment of mice with DMBA

DMBA (7, 12-dimethyl benz[α] anthracene) is a potent carcinogen that causes tumor formation on the skins of $C_3B_6F_1$ mice in just over six months of chronic treatment. Because of its potency at causing tumors it was chosen as the first compound to test in animals for the change in pattern of gene expression following a short period, two weeks, of carcinogen treatment.

Approximately 5-sq. cm area was shaved on the backs of $C_3B_6F_1$ mice. Three males and three females were treated for ten weekdays with 250 μg of DMBA in 100 μl of acetone. Controls were treated with 100 μl acetone alone.

The next weekday following the tenth treatment, the animals were sacrificed and the following tissues removed and flashed frozen in liquid nitrogen; treated skin, liver, bladder, lungs, and stomach.

2. Differential gene expression in mouse skin treated with DMBA

Since the treated tissue is the site of maximum tumor formation, this tissue was examined first. Total RNA was extracted from skin by the Trizol acid phenol procedure after grinding the tissue to a powder in liquid nitrogen. PolyA RNA was isolated with oligeotex mRNA kit™ (QIAGEN).

Radiolabeled cDNA was prepared from pooled DMBA treated skin PolyA$^+$ RNA and from the pooled control PolyA$^+$ RNA, as discussed supra. Approximately equal amounts of each was hybridized to an Atlas™ membrane, the filter was washed, and exposed to X-ray film.

After development of several exposures the films were compared and a treated film and control film with approximately equal hybridization for the housekeeping genes were compared to determine which of the 588 mouse sequences on the filter are overexpressed or underexpressed following treatment. Genes found to be overexpressed and suppressed in DMBA treated skin are presented in Table 5.

TABLE 5

Differentially Expressed Genes in DMBA-Treated Mouse Skin Identified by Hybridization with Mouse Atlas ™ cDNA Array Membranes

| Overexpressed Genes | Suppressed Genes |
| --- | --- |
| IGFBP-2; insulin-like growth factor binding protein 2 | RNA polymerase I termination factor TTF-1 |
| HSP84 | ERp72; disulfide isomeraserelated protein |
| Cf2r; thrombin receptor | Etoposide induced p53 responsive (E124) mRNA |
| Inhibitor of the RNA-activated protein kinase | Grp78; glucose regulated protein |
| Limphotoxin receptor | Glutathione S-transferase |
| Laminin receptor 1 | Glutathione S-transferase Mu 1 |
| snoN; ski-related oncogene | Butyrate response factor 1 |
| Neuoleukin | Egr-1 Zn-finger protein |
| Placental Rnase inhibitor | HMG 14 |
| Serine protease inhibitor 2 (spi-2) | Nuclear factor related to P45 NF-E2 |
| | Split hand/foot gene |
| | Transcription factor S-II |
| | IGFBP-4; insulin-like growth factor binding protein 4 |
| | Interleukin 15 |

Differential gene expression in DMBA-treated mouse skin was also probed by hybridization with Mouse Gene Discovery Arrays (GDA) (Genome Systems, Inc.) containing 18,378 double-spotted none-redundant mouse cDNA clones chosen from the I.M.A.G.E. collection. 2.5 μg of polyA$^+$-RNA from DMBA-treated and control mouse skin was used for cDNA labeling and hybridization with two GDA membranes according to the manufacturer instructions, and obtained PhosphorImager files were sent to and analyzed by Genome Systems, Inc. service. As shown in Table 6, 599 cDNA clones display 3 or more fold differences in expression in DMBA-treated skin compared to acetone-treated skin among clones with top 1000 scores (calculated by multiplying ratio of hybridization intensity on difference in average—for two spots—hybridization intensity for corresponding cDNA clones; hybridization intensity for cDNA clones was normalized for intensity of hybridization of control DNA spots).

TABLE 6

Number of cDNA Clones with Changes in Expression in DMBA-Treated Mouse Skin

|  | Number of Genes | |
| --- | --- | --- |
| Difference in Expression | Overexpressed | Suppressed |
| More than 3-fold | 285 | 122 |
| More than 5-fold | 50 | 24 |
| More than 9-fold | 12 | 6 |

3. Differential gene expression in livers of DMBA treated mice

RNA was extracted from mouse liver, which had been previously ground into a fine powder in liquid nitrogen. Poly(A)+ RNA was prepared from total RNA and radiolabeled cDNA prepared, as discussed supra. The cDNAs from the liver of a control animal and a treated animal were each hybridized to an Atlas™ membrane and the differential pattern of gene expression deduced. While initially the filters showed little or no differential expression, upon more careful examination differential expression was observed indicating that the DMBA or a derivation of it had reached the liver and caused changes in gene expression. These results are presented in Table 7.

TABLE 7

Differentially Expressed Genes in Liver of DMBA-Treated Mice Identified by Hybridization With Mouse Atlas ™ cDNA Array Membranes

| Overexpressed Genes | Suppressed Genes |
| --- | --- |
| p53 protein | Cyclin A |
| Lfc proto-oncogene | Prothymosin alpha |
| CSF-1 | Cf2r; coagulation factor II (thrombin) receptor |
| Cdk4 | CRE-BP1; cAMP response element binding protein 1 |
| Heat shock protein 84KD | Gluthathione S-transferase (microsomal) |
| Etoposide induced p53 responsive (E124) mRNA | Elf-1 Ets family transcription factor |
| I-Kappa Beta | HMG-14 |
| SP13; serpin | HomeoBox protein 2.5 |
| CACCC Box binding protein BKLF | Follostatin |

TABLE 7-continued

Differentially Expressed Genes in Liver of DMBA-Treated Mice Identified by Hybridization With Mouse Atlas ™ cDNA Array Membranes

| Overexpressed Genes | Suppressed Genes |
| --- | --- |
| Homeo box protein 8 | Membrane type matrix metalloproteinase |
| Interleukin-2 receptor gamma chain | |
| Glucocorticoid receptor form A | |
| Bone morphogenetic protein 1 | |
| Cathepsin D | |
| Cathepsin L | |
| Collagenase type IV | |

EXAMPLE 3

Gene Expression Changes in Liver of Mice Treated with Furan and Trichloroethylene 1. Treatment of mice with Carcinogens.

Furan and trichloroethylene (TCE) are shown to induce hepatocellular carcinomas in mice; both are negative in Salmonella mutagenicity test though furan induces gene mutations, and sister chromatide exchanges and chromosomal aberrations in mammalian cells in vitro. $C_3B_6F_1$ Mice were treated with either furan (30 mg/kg/dose) or TCE (2400 and 1800 mg/kg/dose for males and females respectively) by gavage in corn oil. The control mice were treated with corn oil alone. The study contained ten animals of each sex in each treated and control group. The treatment was carried out for ten working days, with no treatment on weekend days for the carcinogen-treated animals and for nine days of control group. The treatment was carried out for ten working days, with no treatment on weekend days for the carcinogen-treated animals and for nine days for control group. Animals were sacrificed humanely and tissues were snap-frozen inl liquid nitrogen.

2. Differential gene expression in liver of mice trated with furan and TCE. Total and (polyA+) RNAs isolation, labeling of cDNA, hybridization with Atlas™ cDNA Expression Arrays (Clontech) and analysis of the hybridization results were performed as described above for differential gene expression in DMBA-treated mouse skin. List of genes that showed changes in expression in liver of furan and TCE-treated mice is presented in Table 8.

TABLE 8

Differentially Expressed Genes in Liver of Mice Treated with Furan and Trichloroethylene

| Overexpressed Genes | | Suppressed Genes | |
| --- | --- | --- | --- |
| Furan Treated Liver | TCA Treated Liver | Furan Treated Liver | TCA Treated Liver |
| Heat Shock Protein 27KD | | Insulin-Like Growth Factor-Binding Protein 2 | |
| | Golgi 4 Transmembrane Spanning Transporter | Prothymosin alpha | Prothymosin alpha |
| Protein Kinase C theta | Protein Kinase C theta | Tob Antiproliferative Factor | |
| Rab-2 Ras Related Protein | Rab-2 Ras Related Protein | Heat Shock Protein 86 | Heat Shock Protein 86 |
| Rac 1 Murine Homologue | Rac 1 Murine Homologue | Erp72 ER Stress Protein | Erp72 ER Stress Protein |
| Glutathione S-Transferase A | Glutathione S-Transferase A | Etoposide Induced p53-Responsive (E124) mRNA | Etoposide Induced p53-Responsive (E124) mRNA |
| Glutathione S-Transferase Mu 1 | Glutathione S-Transferase Mu 1 | Glucose-Regulated Protein 78KD | Glucose-Regulated Protein 78KD |
| Nuclear Factor Related to NF-E2 | Nuclear Factor Related to NF-E2 | Oxidative Stress-Induced Protein | Oxidative Stress-Induced Protein |
| Split Hand/Foot Gene | Split Hand/Foot Gene | Inhibitor of RNA-Activated Protein Kinase 58KD | Inhibitor of RNA-Activated Protein Kinase 58KD |
| Integrin beta | | Microsomal Glutathione S-Transferase | Microsomal Glutathione S-Transferase |

TABLE 8-continued

Differentially Expressed Genes in Liver of Mice Treated with Furan and Trichloroethylene

| Overexpressed Genes | | Suppressed Genes | |
|---|---|---|---|
| Furan Treated Liver | TCA Treated Liver | Furan Treated Liver | TCA Treated Liver |
| CamK II Protein Kinase | CamK II Protein Kinase | Glutathione S-Transferase Pil | Glutathione S-Transferase Pil |
| CDC42 GTP-Binding Protein | | Lymphocyte-Specific NGF Receptor Family Member CD27 | Lymphocyte-Specific NGF Receptor Family Member CD27 |
| Cytokeratin 18 | Cytokeratin 18 | Apolipoprotein J (Clusterin) | Apolipoprotein J (Clusterin) |
| | | DAD-1; Defender against Cell Death 1 | DAD-1; Defender against Cell Death 1 |
| | | TDAG51 | |
| | | PA6 Stromal Protein (RAG1 Gene Activator) | |
| | | MHR23B; Rad23 Homologue | |
| | | Butirate Response Factor 1 | |
| | | Transcription Factor S-II | Transcription Factor S-II |
| | | C5A Receptor | C5A-Receptor |
| | | Bone Morphogenetic Protein 1 | Bone Morphogenetic Protein 1 |
| | | Insulin-Like Growth Factor-Binding Protein 4 | Insulin-Like Growth Factor-Binding Protein 4 |
| | | Neuroleukin | |
| | | Cathepsin H | Cathepsin H |
| | | Cathepsin L | Cathepsin L |

What is claimed is:

1. An assay for early detection of carcinogenesis, comprising the steps of:
   a) preparing cDNA from RNA isolated from mammalian cells treated with a test agent, wherein said test agent is not a known carcinogen, for less than about two years, wherein said cDNA is detectably labeled;
   b) determining a pattern of expression by assessing the ability of said labeled cDNA to hybridize to each of a multiplicity of nucleotide sequences arrayed on a substrate;
   c) determining reference patterns of differential gene expression by assessing the ability of a second labeled cDNA to hybridize to each of a multiplicity of nucleotide sequences, wherein said second labeled cDNA is prepared from RNA isolated from mammalian cells treated with a known carcinogen for less than about two years and
   d) comparing similarities in patterns of expression from cells treated with a test agent to reference patterns from cells treated with a known carcinogen.

2. The assay of claim 1, wherein RNA is isolated from mammalian cells treated with said test agent or known carcinogen for less than about six months.

3. The assay of claim 2, wherein RNA is isolated from mammalian cells treated with said test agent or known carcinogen for less than about two weeks.

4. The assay of claim 3, wherein RNA is isolated from mammalian cells treated with said test agent or known carcinogen for less than about two days.

5. The assay of claim 1, wherein said mammalian cells are treated in vitro.

6. The assay of claim 1, wherein said mammalian cells are treated in vivo.

7. The assay of claim 1, wherein said substrate is selected from the group consisting of: membrane filter; glass; ceramic; and solid organic polymer.

8. The assay of claim 1, wherein said detectable label is selected from the group consisting of: radioisotope; fluorescent dye molecule; enzyme; antigen or antibody.

9. The assay of claim 1, wherein said differential gene expression is selected from the group consisting of: genes whose level of expression is increased; genes whose level of expression is decreased; gene that are expressed; and genes that are not expressed.

10. A method to identify a test substance as a carcinogen, wherein said test substance is not a known carcinogen, which method comprises:
    a) providing cDNA derived from mammalian cells that have been contacted with said test substance for less than about two years,
    b) determining a first pattern of hybridization of said cDNA with respect to a multiplicity of nucleotide sequences;
    c) comparing said pattern with a corresponding second pattern obtained at a corresponding time after said cells have been contacted with a known carcinogen, whereby a similarity in said first and second patterns identifies the test substance as a carcinogen.

11. The method of claim 10, wherein cDNA is obtained from said cells hat have been contacted with said test substance or known carcinogen for less than about six months.

12. The method of claim 11, wherein cDNA is obtained from said cells that have been contacted with said test substance or known carcinogen for less than about two weeks.

13. The method of claim 12, wherein cDNA is obtained from said cells that have been contacted with said test substance or known carcinogen for less than about two days.

14. The method of claim 10, wherein said cells are contacted with said test substance or known carcinogen in vitro.

15. The method of claim 10, wherein said cells are contacted with said test substance or known carcinogen in vivo.

16. An assay for early detection of carcinogenesis, comprising the steps of:
    a) selecting protein isolated from mammalian cells treated with a test agent, wherein said test agent is not a known carcinogen, for less than about two years;
    b) measuring differences in protein synthesis or post-translational modification; and
    c) determining whether said test agent is carcinogenic by comparing differences in protein synthesis or post-translational modification to protein isolated from mammalian cells treated with a known carcinogen for less than about two years.

17. The method of claim 16, wherein said differences in protein synthesis or post-translational modification are measured by electrophoretic gel analysis and said protein is detectably labeled.

18. The method of claim 16, wherein said differences in protein synthesis or post-translational modification are measured by enzymatic digestion of protein and mass spectrometry analysis.

19. The method of claim 16, wherein said protein is isolated from said cells treated with said test agent or known carcinogen for less than about six months.

20. The method of claim 19, wherein said protein is isolated from said cells treated with said test agent or known carcinogen for less than about two weeks.

21. The method of claim 20, wherein said protein is isolated from said cells treated with said test agent or known carcinogen for less than about two days.

22. The method of claim 16, wherein said cells are treated with said test agent or known carcinogen in vitro.

23. The method of claim 16, wherein said cells are treated with said test agent or known carcinogen in vivo.

* * * * *

SEQUENCE LISTING

```
<160> NUMBER OF SEQ ID NOS: 19

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1 attaccctc actaaatgct gggga                                      25

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2 attaccctc actaaatcgg tcatag                                     26

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3 attaccctc actaaatgct ggtgg                                      25

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
```

```
attaaccctc actaaatgct ggtag                                      25

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
attaaccctc actaaagatc tgactg                                     26

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
attaaccctc actaaatgct gggtg                                      25

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
attaaccctc actaaatgct gtatg                                      25

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
attaaccctc actaaatgga gctgg                                      25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
attaaccctc actaaatgtg gcagg                                      25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
attaaccctc actaaagcac cgtcc                                      25

<210> SEQ ID NO 11
<211> LENGTH: 30
<212> TYPE: DNA
```

-continued

```
<213> ORGANISM: Artificial Sequence
<220> FEATURE:
<223> OTHER INFORMATION: primer

<400> SEQUENCE: 11
cattatgctg agtgatatct ttttttttaa                                    30

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
cattatgctg agtgatatct ttttttttac                                    30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
cattatgctg agtgatatct ttttttttag                                    30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
cattatgctg agtgatatct ttttttttca                                    30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
cattatgctg agtgatatct ttttttttcc                                    30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
cattatgctg agtgatatct ttttttttcg                                    30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
cattatgctg agtgatatct ttttttttga                                    30
```

```
<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
cattatgctg agtgatatct ttttttttgc                                              30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
cattatgctg agtgatatct ttttttttgg                                              30
```